(12) United States Patent
Hikichi

(10) Patent No.: US 7,685,701 B2
(45) Date of Patent: Mar. 30, 2010

(54) METHOD AND APPARATUS FOR RESTORING ALIGNMENT OF THE SUPPORT SOCKET IN THE MANUFACTURE OF LEG PROSTHESES

(76) Inventor: Yuichi Hikichi, 110 Kamiyanagi, Yamagata-shi, Yamagata (JP)

(*) Notice: Subject to any disclaimer, the term of this patent is extended or adjusted under 35 U.S.C. 154(b) by 1532 days.

(21) Appl. No.: 10/904,607

(22) Filed: Nov. 18, 2004

(65) Prior Publication Data
US 2006/0106465 A1 May 18, 2006

(51) Int. Cl.
*B23P 21/00* (2006.01)
*B23Q 15/00* (2006.01)

(52) U.S. Cl. .......................... 29/721; 29/464; 29/281.5

(58) Field of Classification Search .................. 29/464, 29/720, 721, 281.5; 623/33, 901
See application file for complete search history.

(56) References Cited

U.S. PATENT DOCUMENTS

| | | | | |
|---|---|---|---|---|
| 4,821,200 A * | 4/1989 | Oberg | ........................ | 700/182 |
| 4,923,476 A * | 5/1990 | Cooper et al. | ................. | 623/38 |
| 5,127,420 A * | 7/1992 | Horvath | ...................... | 600/595 |
| 5,432,703 A * | 7/1995 | Clynch et al. | ............... | 700/163 |
| 5,539,649 A | 7/1996 | Walsh | ................... | 364/474.05 |
| 5,901,060 A | 5/1999 | Schall | ................... | 364/468.04 |
| 5,904,721 A | 5/1999 | Henry | .......................... | 623/26 |
| 6,113,642 A | 9/2000 | Petrofsky | ..................... | 623/24 |
| 6,144,386 A | 11/2000 | Pratt | .......................... | 345/425 |
| 6,317,980 B2 * | 11/2001 | Buck, III | ................. | 29/897.31 |
| 6,463,351 B1 | 10/2002 | Clynch | ........................ | 700/163 |
| 7,240,414 B2 * | 7/2007 | Taylor, Sr. | ................. | 29/527.1 |
| 2003/0195623 A1 | 10/2003 | Marchitto | ....................... | 623/7 |
| 2003/0236473 A1 | 12/2003 | Dore | ........................... | 600/587 |
| 2004/0068337 A1 * | 4/2004 | Watson et al. | ................. | 700/98 |
| 2006/0020348 A1 * | 1/2006 | Slemker et al. | ............... | 623/33 |
| 2007/0039152 A1 * | 2/2007 | Maekawa et al. | .......... | 29/407.1 |

FOREIGN PATENT DOCUMENTS

| | | |
|---|---|---|
| DE | 4232606 | 3/1994 |
| EP | 88302527.2 | 9/1988 |
| GB | 9120977.5 | 4/1992 |

\* cited by examiner

*Primary Examiner*—David P Bryant
*Assistant Examiner*—Christopher M Koehler
(74) *Attorney, Agent, or Firm*—Seth M. Reiss, AAL, ALLLC; Seth M. Reiss

(57) ABSTRACT

An apparatus for restoring the alignment of the support socket with other structural components during the fabrication of a leg prosthesis comprising a stand with base, a means to secure the lower aspect of the leg prosthesis to the stand base, and a laser source attached to the top of the stand that emits visible cross-beams downward onto the leg prosthesis when the prosthesis is mounted on the stand base. The method of the invention uses the described apparatus with leg prosthesis mounted thereon to mark points on the inside of a check or test socket that coincide with the laser cross-beams; transferring these marks from the check socket to the permanent support socket; and re-aligning the permanent support socket with the lower aspect prosthetic components by mounting the leg prosthesis with permanent support socket on the alignment apparatus and matching the marks to the laser cross-beams. A removable base plate allows for a number of leg prostheses to be fabricated concurrently, using the same alignment apparatus. The method and apparatus of the present invention reduces the time and expense of orthotic fabrication while increasing the accuracy of alignment of the finished prosthetic product.

10 Claims, 4 Drawing Sheets

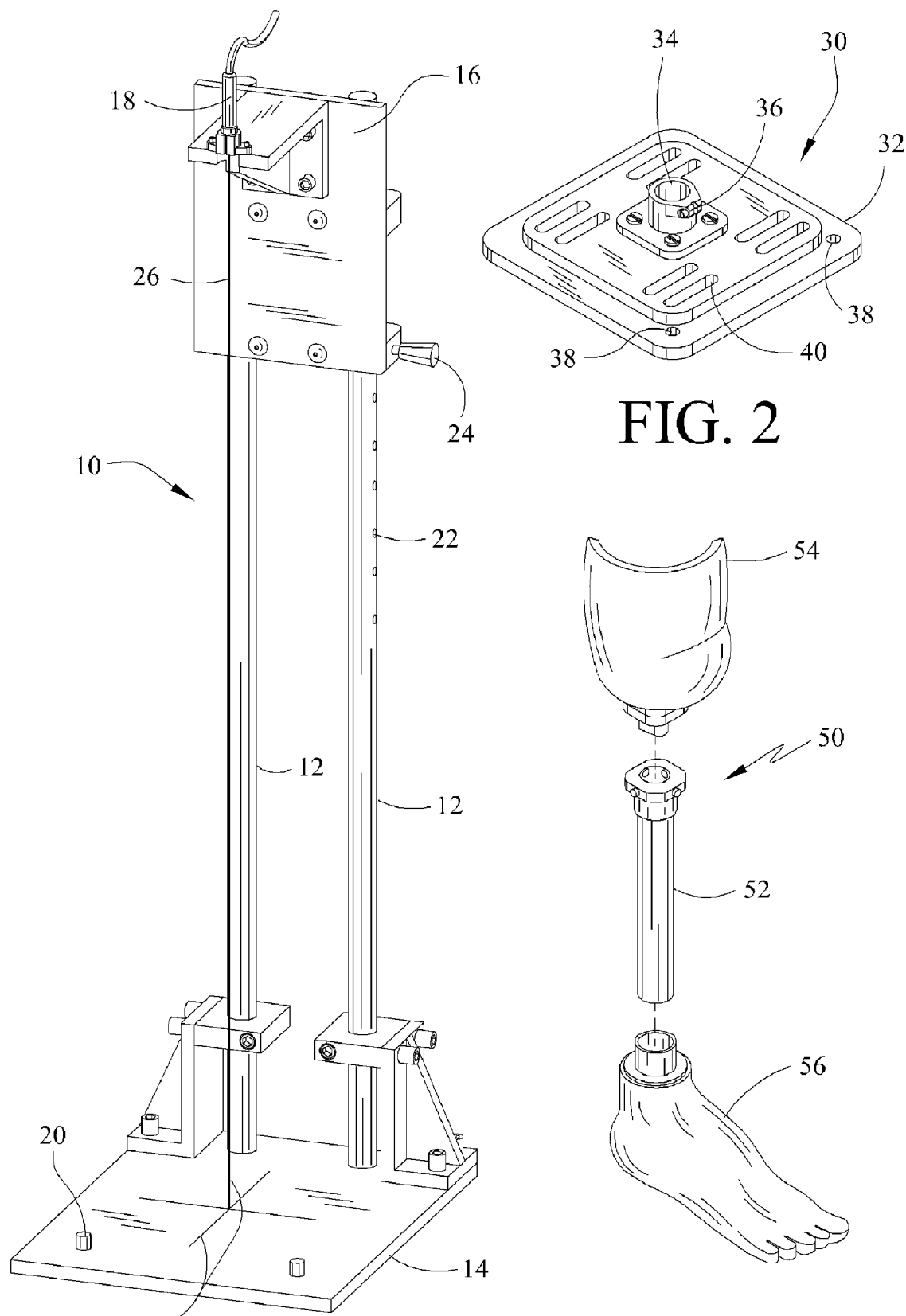

METHOD AND APPARATUS FOR RESTORING ALIGNMENT OF THE SUPPORT SOCKET IN THE MANUFACTURE OF LEG PROSTHESES

CROSS-REFERENCE TO RELATED PATENT APPLICATIONS

This application does not claim the benefit of any related patent application.

STATEMENT REGARDING FEDERALLY SPONSORED RESEARCH OR DEVELOPMENT

The subject invention is not the result of or in any way related to federally sponsored research or development.

FIELD OF INVENTION

This invention relates to the fabrication of prosthetic limbs. More particularly, this invention describes a method and apparatus for restoring the alignment of structural components of leg prostheses during the fabrication process.

BACKGROUND OF INVENTION

Leg prostheses come in three general varieties: hip disarticulation prostheses comprising a socket, hip joint, knee joint and foot; above-knee prostheses comprising a socket, knee joint and foot; and below-knee prostheses comprising just the socket and foot. In each case, a stump or support socket, or just socket, to receive the leg stump must be fabricated and correctly aligned with the other prosthetic components that extend downward there from.

The conventional process of fabricating and fitting the stump socket is typically as follows: A check or test socket mold or model is cast from a malleable material, typically plaster or plastic, directly from the amputees stump. The check or test socket is fitted on the remaining prosthetic components for fitting or "trial walking". During trial walking, the check socket is aligned with the adjacent prosthetic component using a jig, and the alignment marked. Through a process similar to the casting of a sculpture, a positive impression or model is cast from the check socket, and then the positive model is used to cast the definitive, or permanent, support socket. After fabrication of the permanent support socket, it becomes necessary to restore the alignment of the permanent socket with the other prosthetic components.

The fabricating process is labor intensive, time consuming, specialized and expensive. Competent orthotic technicians are highly skilled craftsmen with extensive training and experience. The fabrication, assembly and alignment process often involves trial and error and much depends upon the judgment and skill of the artisan fabricator.

Fabrication and proper assembly of the support socket is the most delicate and time consuming aspect of the leg prosthesis fabrication process. Support sockets made for above-knee prosthetics are larger, more difficult to fabricate, and less forgiving than those for below-knee prosthetics. In each case, however, re-alignment of the permanent socket with the lower orthotic components is necessary. Support sockets that are not properly shaped, or inexactly aligned, are uncomfortable to use and can cause damage or injury to the patient's stump, requiring that the socket be re-aligned or re-fabricated.

A number of inventions have been described having as their object the improved fabrication of lower limb prostheses. Most teach the use of computers and computer imaging to shape and/or orient the support socket, to fabricate the permanent socket, or to map or locate bony protuberances in the stump. Other inventions describe apparatus that facilitate the casting of the temporary socket or fabrication of the permanent socket. All such inventions have as their goal making the fabrication process less labor intensive, less time consuming, less expensive or more exacting.

One of the more time consuming and difficult aspects of the process of fabricating lower limb orthotic devices is the need to precisely re-align the permanent support socket with the adjacent structural component after the definitive socket is cast. The initial alignment is marked during the trial walking phase, but this alignment is lost when the check socket is transformed into a positive model and then transformed, a further time, into the permanent socket.

Presently the process of restoring the alignment of the definitive socket with the other prosthetic components is accomplished by transferring lines and points from the check socket, to the positive model, and then again from the positive model to the permanent socket. Due to the thickness and three-dimensional shape of the support socket, the process of transferring the reference points is difficult, cumbersome and time consuming. Drilling and the use of alignment benches or stands having screw adjusters are used to facilitate the process. Even with these aids, however, points are not transferred accurately, causing the resulting alignment to be inexact and requiring that the process be repeated or begun again. None of the prior art publications or commercially available apparatuses fully addresses the difficulty in restoring the alignment of the definitive support socket in the leg prosthesis fabrication process.

It is a primary object of the present invention to provide a method and apparatus to facilitate the restoration of alignment of the permanent support socket with the adjacent prosthetic component during the fabrication process. It is a further objection of the present invention to provide a method and apparatus to restore the alignment of the support socket of a leg prosthesis during the fabrication process that improves the precision of alignment, and that increases the speed and accuracy with which leg prostheses are produced while reducing the cost of their production. It is also an object of the present invention to provide a method and apparatus for the fabrication and re-alignment of multiple support sockets concurrently, using the same apparatus.

SUMMARY OF INVENTION

These and other problems are solved by the instant invention, a method and apparatus for restoring the alignment of newly fabricated support sockets with the other structural components of leg prostheses. The novel apparatus comprises a stand assembly with a laser source affixed at the top of the assembly pointing downward, and having a removable base plate on the bottom of the stand assembly that can be adjusted using tightening screws.

The stand assembly receives the leg prosthesis with its lower aspect secured to the removable plate. The prosthesis is centered within the apparatus using the tightening screws. The laser source emits visible laser cross-beams downward towards the base of the assembly such that the cross-beams are exhibited within the cavity of the stump socket. A jig may be affixed between the socket and lower prosthetic components to facilitate orientation of the socket relative to the adjacent prosthetic component.

The method of the invention is as follows: A leg prosthesis with check socket aligned to the other prosthetic components through the use of a jig and the process of trial walking is mounted and secured on the stand assembly such that the support socket is roughly centered beneath the laser source. The laser source is turned on resulting in cross-beams being exhibited across the inside of the support socket. Points are marked on the inside surface of the check socket that coincide with the cross-beams. Typically five points are marked, one at each extreme of the cross-beams and one at the point where the cross-beams intersect.

The prosthesis is then disassembled and a permanent socket is fabricated through the process of making a positive model. The points marked on the temporary socket are transferred, using special marking pens, dimpling tools, and/or drilling, to the positive model. A permanent socket is then fabricated from the positive model and the points are once again transferred, using the same marking methods, from the positive model to the permanent socket.

Alignment of the permanent socket with the lower prosthetic components is restored by mounting the permanent socket together with the other prosthesis components on the stand assembly, illuminating the laser, and matching the marks that were transferred from the check socket to the permanent socket against the laser cross-beams that appear across the inside of the permanent socket.

The removable base allows several leg prostheses to be manufactured and aligned at the same time using the one apparatus. The stand can be made height adjustable to accommodate leg prostheses of different lengths.

This new apparatus and method allows for more rapid prosthetic fabrication with greater precision in alignment of the socket component, saving fabricators time and money, and allowing for the production of more precise leg prostheses at a lower cost.

BRIEF DESCRIPTION OF THE DRAWINGS

FIG. 1 is a perspective view, from the front, of the alignment apparatus of the present invention without base plate.

FIG. 2 is a top perspective view of an adjustable base plate that mounts on the base of the alignment apparatus shown in FIG. 1.

FIG. 3 is an exploded view of the structural components of a typical below-knee leg prosthesis.

DETAILED DESCRIPTION OF PREFERRED EMBODIMENTS

Figure 4:
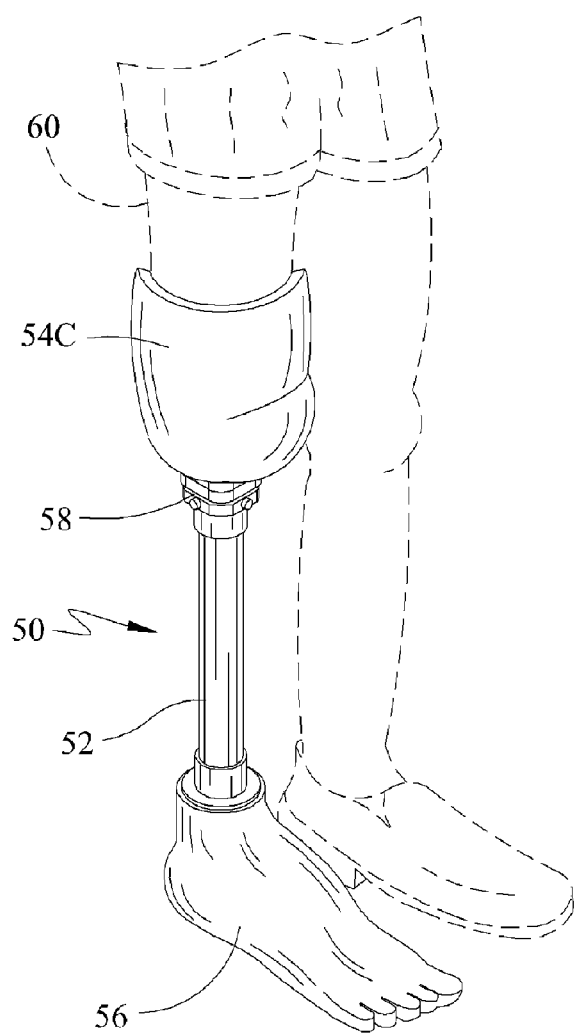
FIG. 4 is a perspective view of the below-knee leg prosthesis of FIG. 3 assembled being worn by a patient for trial walking.

The alignment apparatus of the present invention is illustrated from the front in FIG. 1. Alignment apparatus 10 comprises a stand 12 with a base 14. A bracket 16 affixed to the top of stand 12 extends forward from the top of stand 12 and is used to mount a laser source 18 that points downward. Two base pins 20 attached to the top surface of base 14 are received by and hold in place the removable base plate 30 that is described with reference to FIG. 2.

Apparatus 10 is made height adjustable by way of a plurality of holes 22 drilled along the upper portion of the length of stand 12. Holes 22 receive a spring-loaded stand pin 24. Bracket 16 can slide up and down along stand 12. Bracket 16 is secured at given heights along stand 12 using stand pin 24 together with pin holes 22. Other known manners of making stand 12 height adjustable, although not illustrated here, are within the scope of the present invention.

Laser source 18 is shown illuminated in FIG. 1 emitting a cross-beam 26 downward onto base 14. Whereas laser 18 in FIG. 1 emits downward a single cross-beam 26, laser sources that emit three or more beams that intersect at a single point can also be employed to provide additional points of reference.

Shown in FIG. 2 from the top is a removable base plate 30 designed to overlay and lock into place on base 14 of the alignment apparatus 10 shown in FIG. 1. According to the embodiment shown, base plate 30 is comprised of a double layer plate 32. A leg mount 34 equipped with a tightening device 36 is affixed to the top middle of plate 32.

Drill holes 38 in the lower layer of plate 32 are positioned to accept pins 20 of apparatus 10 shown in FIG. 1. A plurality of adjusting slots 40 are formed in plate 32 and are used in conjunction with tightening bolts (shown in FIGS. 8 and 9) to center base plate 30 on base 14 of apparatus 10.

While removable base plate 30 illustrated in FIG. 2 is comprised of a double layer plate 32 having adjusting slots 40, base plate 30 can take on a variety of forms that allows plate 30 to be removably locked onto base 14 while remaining sideways adjustable with reference to the top surface of base 14.

The main components of a below-knee prosthetic leg 50 are illustrated, in exploded view, in FIG. 3. Below-knee prosthesis 50 is comprised of an artificial leg or pylon 52 interposed between a support socket 54 and an artificial foot 56. Support socket 54 could be a check or test socket, or a definitive or permanent socket. Proper alignment of support socket 54 with pylon 52 and foot 56 is critical to the proper functioning of leg prosthesis 50 and the comfort and health of the patient that uses leg prosthesis 50.

Below-knee prosthesis 50, fitted on a patient, is illustrated in perspective view in FIG. 4. The lower end of pylon 52 is secured within artificial foot 56. A check or test socket 54C is secured to the top end of pylon 52, shown here through a jig 58. Check socket 54C receives and encloses a patient's stump 60.

FIG. 4 also illustrates the fitting phase of leg prosthesis fabrication sometimes referred to as trial walking. Check socket 54C is aligned with lower prosthetic components 52 and 56 for correct support and comfort. Proper alignment is achieved through the use of jig 58, an adjusting apparatus interposed between check socket 54C and the adjacent prosthetic component that, in FIG. 4, is pylon 52. Jig 58 is used to adjust the alignment of check socket 54C with pylon 52 while the patient stands and walks, until the optimal alignment is reached. Once correctly aligned, alignment apparatus 10 is used to enable the fabricator to re-establish this optimal alignment after the definitive support socket has been cast.

Figure 5:
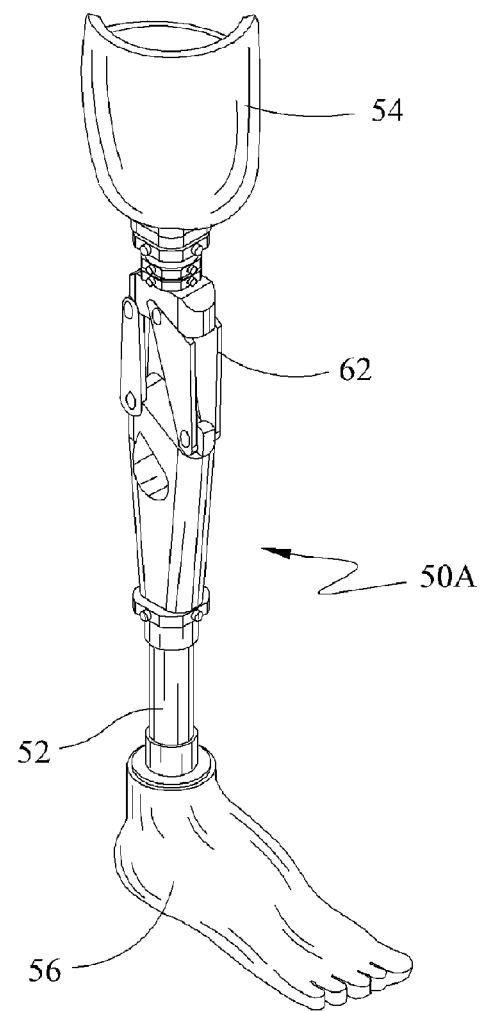
FIG. 5 is a perspective view of an above-knee prosthesis assembled and ready to wear.

Depicted in FIG. 5 is above-knee prosthesis 50A shown in assembled form. Above-knee prosthesis 50A is comprised of support socket 54 attached to an artificial knee 62 which, in turn, is supported by pylon 52 attached to artificial foot 56.

Artificial knee 62 shown in FIG. 5 includes mechanical linkages reflecting a variety of artificial knee joint termed polycentric knees. Other varieties of artificial knee joints are well known and commercially available, including those controlled by friction, hydraulics and/or micro-computer systems. The apparatus and method of the instant invention can be employed with any and all varieties of artificial knee joints with similarly advantageous results.

Figure 6:
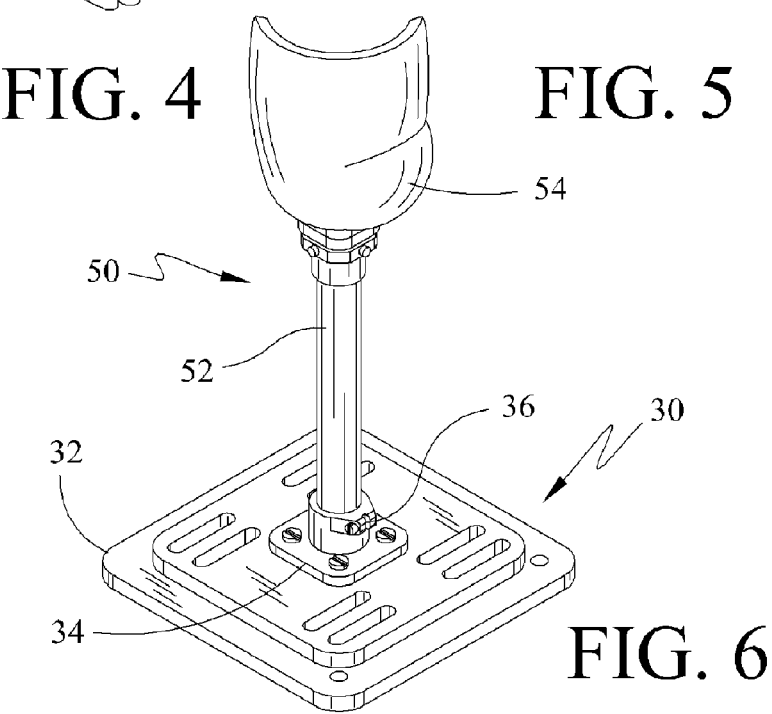
FIG. 6 is a perspective view of the below-knee prosthesis of FIG. 3, without foot attached, mounted on the base plate of the alignment apparatus of the present invention.
Figure 7:
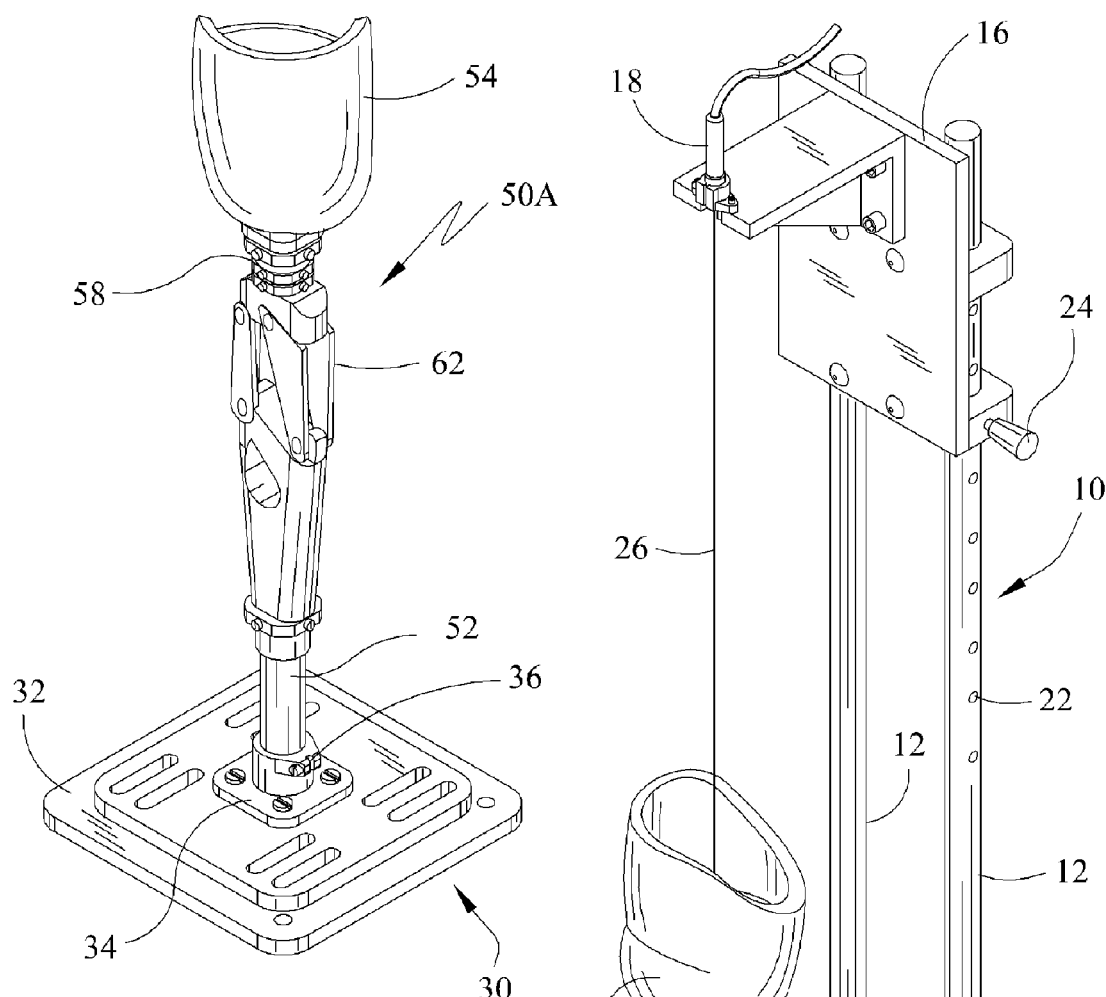
FIG. 7 is a perspective view of the above-knee prosthesis of FIG. 5, without foot attached, mounted on the base plate of the alignment apparatus of the present invention.

FIGS. 6 and 7 illustrate below-knee leg prosthesis 50 and above-knee leg prosthesis 50A, respectively, mounted on adjustable base plate 30. In both instances artificial foot 56 has been removed from pylon 52. Also in both instances the bottom end of pylon 52 has been inserted into leg mount 34 and secured therein using tightening device 36. Above-knee prosthesis 50A is shown in FIG. 7 with jig 58 interposed between socket 54 and artificial knee 62. Once secured onto base plate 32, leg prosthesis 50 or 50A with base plate 32 can be secured on base 14 of alignment apparatus 10.

Figure 8:
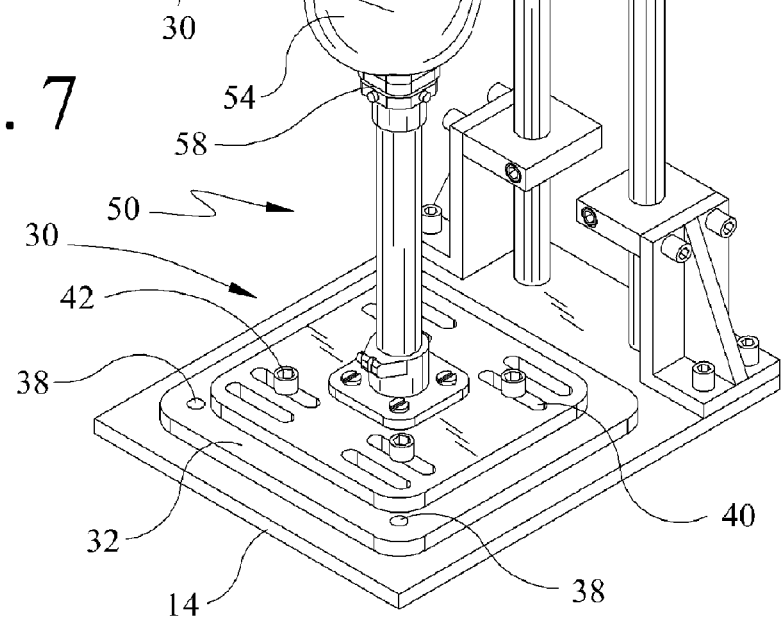
FIG. 8 is a front perspective view of the alignment apparatus of the present invention with the below-knee leg prosthesis of FIG. 3 mounted thereon and with the laser source illuminated.
Figure 9:
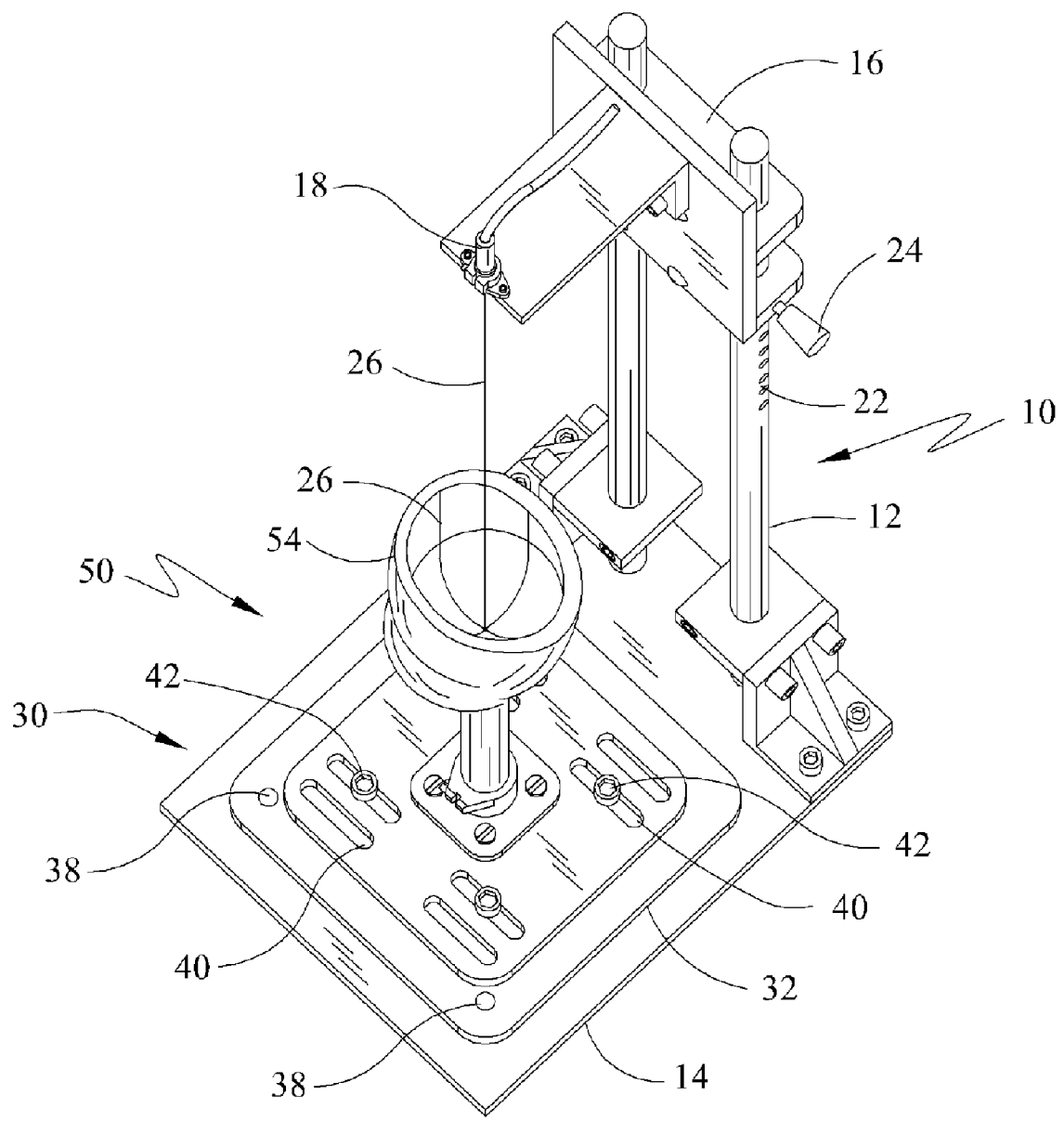
FIG. 9 is a top perspective view of the alignment apparatus of the present invention with the below-knee leg prosthesis of FIG. 3 mounted thereon and with laser illuminated.

FIG. 8 depicts from the front, and FIG. 9 from above, prosthetic leg 50 mounted on alignment apparatus 10 with laser source 18 emitting cross-beams 26 downward into the inside surface of support socket 54.

Referring to both FIGS. 8 and 9, the height of stand 12 is adjusted to accommodate the length of prosthetic leg 50 by sliding and securing bracket 16 along stand 12 using holes 22 and stand pin 24. Prosthetic leg 50, secured to base plate 30 without foot 56, is mounted on apparatus 10 by positioning holes 38 to receive base pins 20 (shown in FIG. 1). Leg 50 can be centered within the top surface of base 14 by sliding the layers of base plate 32 along slots 40 and then tightening the layers one to the other using a plurality of tightening bolts 42.

Also illustrated in FIGS. 8 and 9 is laser 18 emitting laser cross-beams 26 downward onto the inside surface of support socket 54. As can be seen in FIG. 9, laser cross-beams 26 transverse the entire inside surface of socket 54, intersecting in the center, for ease of marking.

The method of the present invention is illustrated with reference to FIGS. 3 through 9. A check or test socket 54C is fabricated through the casting process and assembled with the lower components of leg prosthesis 50 or 50A (FIGS. 3 and 5). Alignment of test socket 54C with the lower leg prosthetic components is achieved through adjustments using jig 58 and trial walking (FIG. 4). Once aligned, leg prosthesis 50 or 50A, without artificial foot 56, is secured onto base plate 30 (FIGS. 6 and 7).

The height of alignment apparatus 10 is adjusted to accommodate the length of leg 50, and leg 50 with base plate 30 attached is secured on base 14 of apparatus 10 (FIGS. 8 and 9). Leg 50 is centered on base 14 using slots 40 and tightening bolts 42. Laser source 18 is illuminated and laser cross-beams 26 are emitted downward and can be visualized across the inside surface of check socket 54C (FIGS. 8 and 9).

The prosthetic technician then marks points along the inside of check socket 54C corresponding to the intersection and extreme portions of laser cross-beams 26. A positive model is fabricated from check socket 54C and the points marked on check socket 54C are transferred to the positive model using special marking pens, dimpling and/or drilling techniques. A definitive or permanent support socket 54 is fabricated from the positive model and the points are again transferred, this time from the positive model to permanent support socket 54, using the same marking pens, dimpling and/or drilling techniques.

Once permanent socket 54 is fabricated and marked, socket 54 is assembled together with the lower components of prosthetic leg 50 or 50A. Jig 58 is optionally interposed between socket 54 and the adjacent prosthetic component. Leg 50 or 50A, with base plate 30 attached, is mounted on base 14 of apparatus 10 (FIGS. 8 and 9). Leg 50 (or 50A) is centered within base 14 and secured thereto using slots 40 and tightening bolts 42. Laser 18 is illuminated and laser cross-beams 26 are emitted downward there from and can be visualized across the inside surface of socket 54 (FIGS. 8 and 9).

Socket 54 is aligned relative to the lower prosthetic components using jig 58 to align the transferred points on the inside surface of socket 54 with the laser cross-beams 26. Proper alignment is marked, jig 58 is removed, and socket 54 is permanently secured to the adjacent structural component with correct orientation.

Because base plate 30 is removable, a number of prosthetic legs 50 can be fabricated concurrently using the same alignment apparatus 10. When fabricating a number of prosthetic legs concurrently, it is convenient and efficient to have more than one base plate 30 for each alignment apparatus 10.

SUMMARY AND SCOPE

Accordingly, it will be appreciated that the apparatus and method of the present intention allows for more rapid prosthetic fabrication with greater precision in alignment of the socket component to the lower aspect components, saving fabricators time and money, and allowing for the production of more precise leg prostheses at a lower cost. Whereas many of the inventions designed to improve the fabrication process of leg prostheses are complex, and many utilize sophisticated and expensive technology, the apparatus and method of the instant invention is straightforward, inexpensive to build, and easy to employ and to maintain.

While present invention has been described in terms of specific structures and embodiments, the invention is not limited to the recited structures and embodiments. By way of example, a variety of known and commercially available means for removably securing leg prosthesis 50 to base plate 30, for removably and adjustably securing base plate 30 within base 14, and for adjusting the height of apparatus 10, may be employed within departing from the spirit of scope of the claimed invention. Similarly, any known method of transferring points from check socket 54C to a positive model, and from the positive model to permanent socket 54, can be employed in addition to the methods described above. Accordingly, the scope of the invention should be determined by the appended claims and their legal equivalents, rather than with reference to any particular example, embodiment or illustration.

What is claimed is:

1. An apparatus for restoring the alignment of the support socket in the manufacture of a leg prosthesis comprising:
   a stand with base;
   a means to removably secure the lower aspect of a leg prosthesis with a support socket centrally onto said base;
   a laser source mounted at the top of said stand oriented downward towards said stand base;
   wherein said laser source emits a plurality of visible intersecting beams downward onto said support socket of the leg prosthesis when said leg prosthesis is secured centrally on said stand base.

2. The apparatus of claim 1 wherein said laser source emits visible cross-beams.

3. The apparatus of claim 1 wherein said means to removably secure the lower aspect of a leg prosthesis centrally onto said stand base comprises a sideways adjustable base plate.

4. The apparatus of claim 3 wherein said base plate is made sideways adjustable by means of slots that receive tightening bolts.

5. The apparatus of claim 1 wherein the stand is height adjustable.

6. A method for restoring the alignment of the support socket in the fabrication process of a leg prosthesis, comprising the steps of:
   a. providing an alignment apparatus having a stand with base, a means to removably secure the lower aspect of a leg prosthesis with a support socket centrally onto said stand base, and a laser source mounted at the top of said stand oriented downward towards said stand base, wherein said laser source emits a plurality of visible intersecting beams downward onto said support socket of the leg prosthesis when said leg prosthesis is secured centrally on said base;
   b. using said securing means to secure the lower aspect of a leg prosthesis having a correctly aligned check support socket, centrally onto said base;
   c. illuminating the laser source;
   d. marking the inside of the check socket at points that coincide with the visible laser beams;
   e. casting a permanent support socket from the check support socket;
   f. transferring the marks from the check socket to the permanent socket;
   g. using said securing means to secure the lower aspect of the leg prosthesis with unaligned permanent socket, centrally onto said base;
   h. illuminating the laser source;
   i. restoring the alignment of the permanent support socket by aligning the transferred marks on the permanent socket with the laser beams.

7. The method of claim 6 wherein said laser source emits visible cross-beams.

8. The method of claim 6 wherein said means to removably secure the lower aspect of a leg prosthesis centrally onto said stand base comprises a sideways adjustable base plate.

9. The method of claim 8 wherein said base plate is made sideways adjustable by means of slots that receive tightening bolts.

10. The method of claim 6 wherein said stand is height adjustable.

* * * * *